United States Patent [19]

Lang et al.

[11] Patent Number: 4,644,948
[45] Date of Patent: Feb. 24, 1987

[54] APPARATUS FOR DOSE MEASUREMENT UPON PHOTOCOAGULATION IN THE FUNDUS OF THE EYE

[75] Inventors: Walter Lang, Koenigsbronn; Gerhard Mueller, Aalen; Eugen Weimer, Essingen, all of Fed. Rep. of Germany

[73] Assignee: Carl-Zeiss-Stiftung, Heidenheim on the Brenz, Fed. Rep. of Germany

[21] Appl. No.: 612,670

[22] Filed: May 22, 1984

[30] Foreign Application Priority Data

May 27, 1983 [DE] Fed. Rep. of Germany ....... 3319203

[51] Int. Cl.$^4$ .............................................. A61B 17/36
[52] U.S. Cl. .................................. 128/303.1; 128/395; 128/398; 219/121 LB; 219/121 LZ
[58] Field of Search ..................... 128/303.1, 395–398, 128/664, 665, 666, 667; 219/121 LZ, 121 LB

[56] References Cited

U.S. PATENT DOCUMENTS

| 3,136,310 | 6/1964 | Meltzer | 128/398 X |
| 3,809,092 | 5/1974 | Abraham | 128/395 X |
| 4,120,293 | 10/1978 | Muckerheide | 128/665 |
| 4,166,695 | 9/1979 | Hill et al. | 128/666 X |
| 4,266,549 | 5/1981 | Kimura | 128/303.1 |
| 4,299,229 | 11/1981 | Enderby | 128/395 |
| 4,305,398 | 12/1981 | Sewa | 128/666 X |
| 4,316,467 | 2/1982 | Muckerheide | 128/303.1 |
| 4,412,543 | 11/1983 | Vassiadie et al. | 128/665 X |

FOREIGN PATENT DOCUMENTS 2108282  5/1983  United Kingdom ............. 128/303.1

OTHER PUBLICATIONS

Heydenreich et al, "Fluo-Angio Photocoagulation . . . ", Jena Review, vol. 19, No. 2, pp. 107-110, 1974.

Primary Examiner—Lee S. Cohen
Attorney, Agent, or Firm—Stonebraker, Shepard & Stephens

[57] ABSTRACT

For determining the proper dose of therapy radiation for photocoagulation at the fundus of the eye, the fluorescent radiation excited by the therapy radiation (laser light) in the fundus of the eye is utilized. The fluorescence intensity passes through a characteristic minimum upon the termination of the coagulation process. Apparatus is disclosed for the detection by measurement of this effect. Optical beam splitters are provided to separate the fluorescent radiation from the therapy radiation. An electronically controlled shutter is provided for the passage and blocking off of the therapy radiation. The shutter is closed when the fluorescence intensity reaches a minimum after commencement of coagulation, or when the radiation reaches a predetermined amount, if this occurs before the fluorescence reaches its minimum.

6 Claims, 7 Drawing Figures

APPARATUS FOR DOSE MEASUREMENT UPON PHOTOCOAGULATION IN THE FUNDUS OF THE EYE

The present invention relates to a method and apparatus for measuring the dosage of radiation (e.g., from a laser) applied to the fundus of an eye, the measurement being responsive at least in part to the amount of photocoagulation produced in the fundus by the radiation.

Photocoagulation in the fundus of the eye is produced either by light from a high-pressure xenon lamp or by light from a laser. Regardless of the light source, effective therapy requires a determination of the amount or dose of the radiant energy used.

Ordinarily, the treating physician uses the resultant white color of the coagulated cell plasma as a subjective measure of the radiation dose absorbed in the fundus of the eye. For an objective determination of the dose, it has been proposed to use the intensity of the back-scattering from the place of coagulation as a measure of the dose of therapy radiation. However, such measurements are also subject to uncertainties because the intensity scattered back from the place of coagulation is dependent upon the cell structure, and cell structures differ greatly, not only from one patient to another but also from place to place on the retina of a single patient. Hence a measurement of back scattering alone can not be used as a basis for a trustworthy objective metering of the amount or dose of radiation which is being applied to the eye.

An object of the present invention is to provide a parameter which can be used reliably for the measurement of the dose upon photocoagulation, and to provide effective apparatus for the determination of this parameter.

This object is achieved, in accordance with the invention, by providing means whereby the fluorescent light excited in the fundus of the eye by the therapy radiation is separated from the therapy radiation and is fed to a photodetector for measurement. A shutter is provided in the ray path, for passing or blocking the radiation as required, and also a beam splitter which sends part of the therapy radiation to a first photodetector and the remaining part to the eye of the patient. There is also another beam splitter which separates the fluorescent radiation emitted by the fundus of the eye from the therapy radiation impinging upon the eye and feeds it to a second photodetector. A cutoff filter is preferably provided between the second beam splitter and the second photodetector.

In one advantageous embodiment of the invention, another beam splitter is provided between the cutoff filter and the second photodetector, this beam splitter permitting direct observation of the coagulation process by the doctor. A deflection mirror provided with a pinhole may also be used for this purpose.

A glass fiber light guide may also be advantageously employed for guidance of the therapy radiation and the fluorescent radiation. This fiber guide may also be conducted or introduced intraocularly for endophotocoagulation. The apparatus for measurement of the dose may be used to particular advantage with slit lamps or operation microscopes.

In one suitable embodiment of the invention, an electronic circuit is provided for opening and closing the shutter to control the passage and blocking or shutting off of the therapy radiation. Also, a time limitation for the dose output may be provided as an additional safety feature.

The advantages resulting from the invention include the fact that the radiation dose necessary for coagulation can be determined objectively from the fluorescent behavior of the pigments present in the blood vessels and the retina, for instance hemoglobin, melanin, and xanthophyll. Thus the intensity of the fluorescence passes, during the coagulation, through a minimum which indicates the termination of the denaturing process and thus constitutes an objective measure for the course of the coagulation.

Differences also occur in the spectral distribution of the fluorescence. If one uses multi-band detection with different wavelengths, it is thus possible to distinguish the place of origin of the fluorescence, since hemoglobin is present as a fluorescent substance primarily in the blood vessels, while melanin and xanthophyll are measured predominantly in the pigment epithelium.

As an example of these conditions, the results of the examination of the absorption and fluorescence behavior of whole blood and blood-perfused tissue during the coagulation are shown in the form of measurement curves.

BRIEF DESCRIPTION OF THE DRAWINGS

In the accompanying drawings, relating to illustrative embodiments of the invention.

DESCRIPTION OF THE PREFERRED EMBODIMENTS

Figure 1:
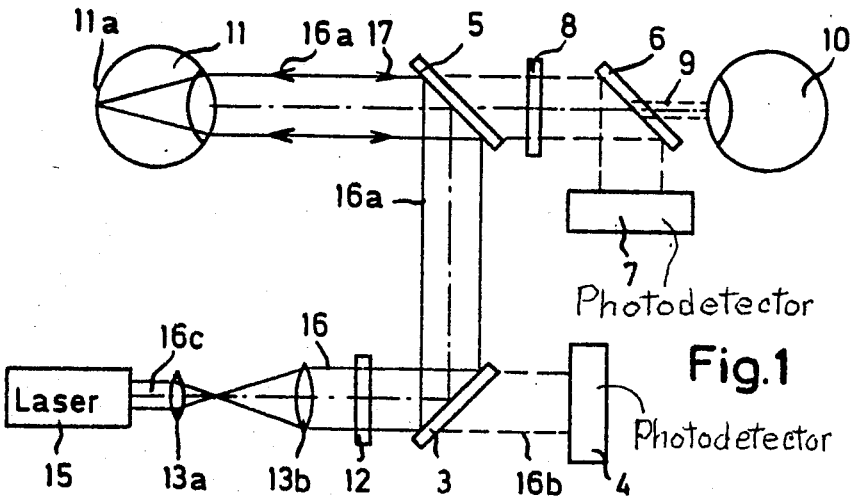
FIG. 1 is a schematic diagram of one form of apparatus providing guidance of the beam in a laser photocoagulator with fluorescence detection.

Referring now to FIG. 1, there is shown somewhat schematically a form of apparatus comprising a laser light source 15 which projects a beam 16c through optical elements 13a and 13b which serve to expand the beam, as shown at 16, to the diameter of the pupil of the eye. This beam 16, a parallel bundle of rays, travels to the shutter device 12 and, when the shutter is open, continues on to a first beam splitter 3, which reflects a portion of the beam, to be used for therapy, to form the therapy beam 16a. The remainder of the beam 16 passes through the splitter 3 to form the beam 16b which goes to a photodetector 4.

The therapy beam 16a is reflected from the beam splitter 3 to a second beam splitter 5, which reflects it into the eye 11 of the patient. Photocoagulation takes place at the fundus 11a. By the irradiation, the hemoglobin contained in the patient's blood and its degradation products are excited to fluorescence. Upon the coagulation, a bleaching out of this fluorescence takes place by the denaturing and masking of the hemoglobin molecules.

The fluorescent light 17 coming from the eye 11 is separated by the beam splitter 5 from the therapy radiation 16a, and is conducted by a mirror 6 to a second photodetector 7. Through a pinhole 9 in the mirror 6, a part of the fluorescent light and of the surrounding illumination passes into the eye 10 of the doctor, enabling him to observe the progress of the treatment. For complete suppression of the therapy radiation so that it does not reach the eye of the observing doctor, a cutoff filter 8 is placed between the beam splitter 5 and the doctor's eye. In the illustrative embodiment, the therapy radiation has a wavelength of 488 nm, and the filter 8 passes wavelengths above 495 nm, cutting off those below.

Figure 2:
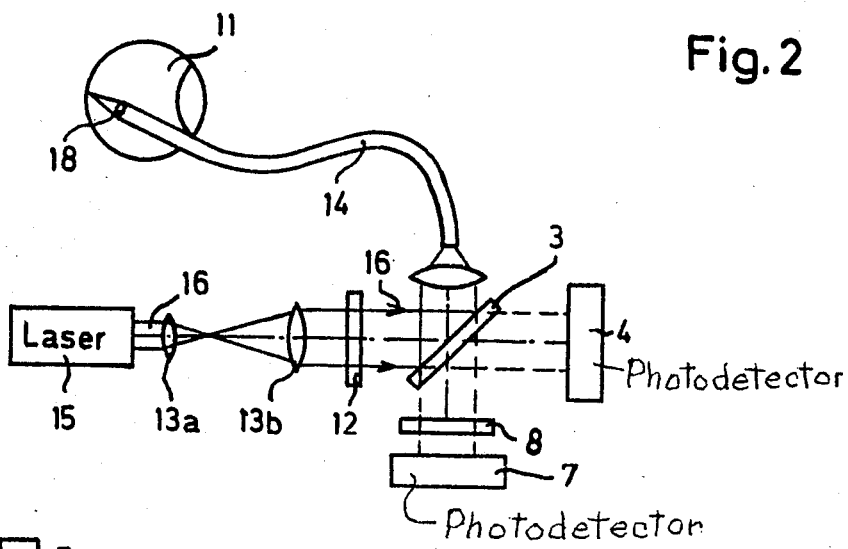
FIG. 2 is a schematic diagram of a second form of apparatus, likewise having guidance of the beam in a laser photocoagulator with fluorescence detection and employing a glass fiber guide for endophotocoagulation.

Another embodiment of the invention is illustrated in FIG. 2. In this embodiment, many of the elements are the same as those in FIG. 1, and operate in the same way, and are designated by the same reference numerals, so that further description of these is unnecessary. This embodiment differs from that in FIG. 1 by the fact that the therapy radiation is conducted by a glass fiber guide 14 with an end lens 18 into the eye of the patient for purposes of endophotocoagulation. The fluorescent light proceeding from the eye is conducted back through the same glass fiber optical guide 14 and is separated by the beam splitter 3 from the therapy radiation 16. An additional cutoff filter 8 is used in front of the photodetector 7. The photodetector 4 measures intensity of the therapy radiation.

Figure 3:
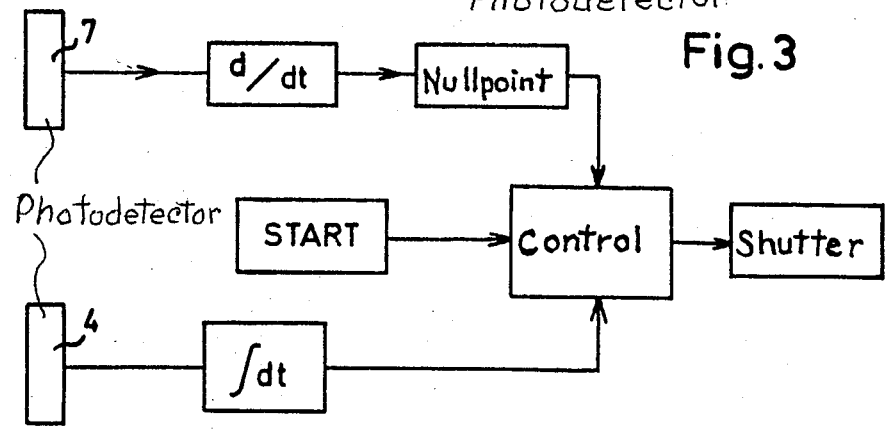
FIG. 3 is a block diagram illustrating electronic circuitry for controlling the shutter for the therapy radiation.

The electronic circuit shown schematically in the block diagram of FIG. 3 serves to control the passage and the blocking or shutting off of the therapy radiation by means of the shutter 12 used in the embodiments of FIGS. 1 and 2. The shutting off of the radiation is to take place after termination of the point coagulation. It is brought about either as soon as a given amount of light (radiation) has entered the eye 11 of the patient (this being a safety disconnect) or when the intensity of fluorescence has reached a minimum. This minimum is determined by an electronic circuit which recognizes the passage through zero of the differentiated fluorescent signal, such circuits being known per se so that the details need not be given here. The therapy radiation measured by the photodetector 4 is integrated with respect to time (dt) by the safety circuit, and the fluorescent light measured by the photodetector 7 is differentiated with respect to time (d/dt).

Figure 4:
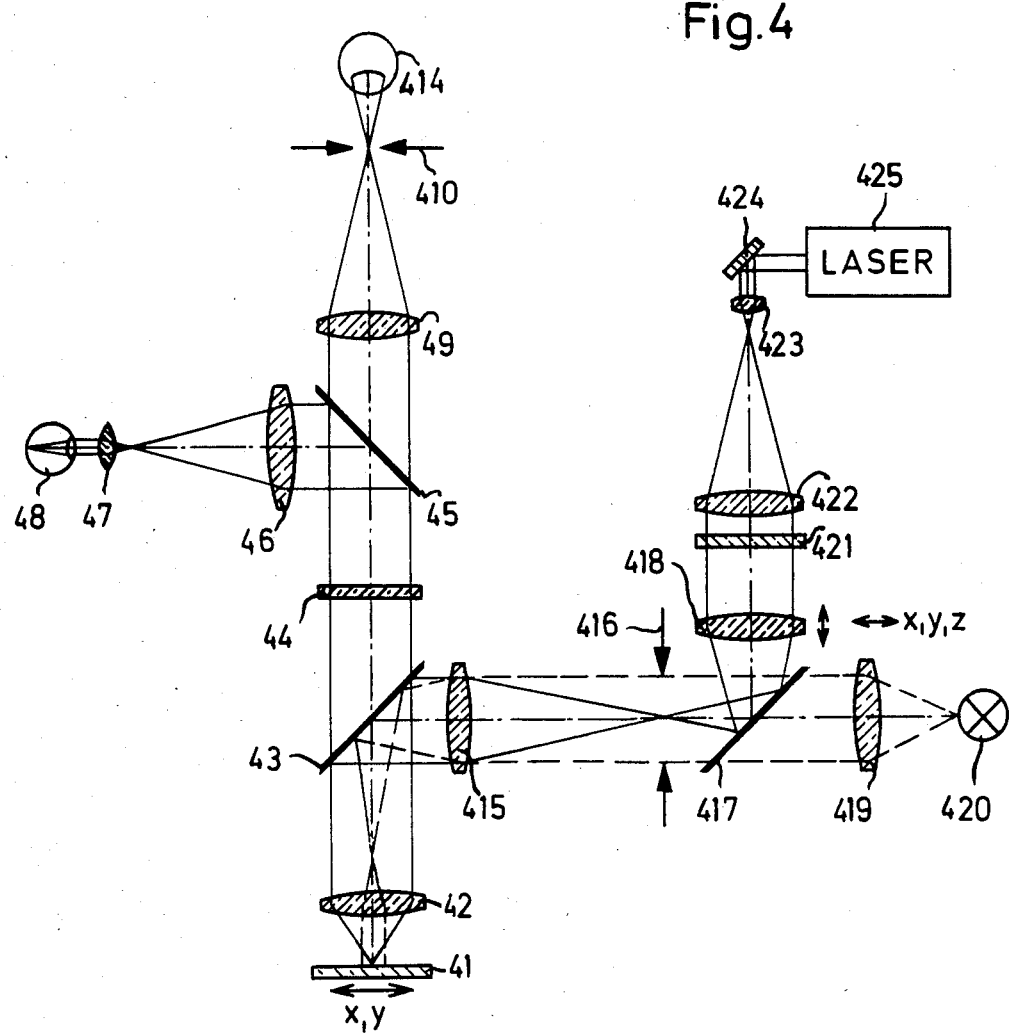
FIG. 4 is a schematic illustration of a laser photocoagulator integrated in a laser microscope.

In the laser microscope shown schematically in FIG. 4, monochromatic light produced by the laser 425 is deflected by a mirror 424, is expanded by the optical elements 423, 422, and 418, and impinges on the chromatic beam splitter 417. Thence the radiation beam is reflected along a path containing a field diaphragm 416 and through an auxiliary lens 415 to another beam splitter 43, which reflects the beam into the microscope axis, where it passes through the microscope objective 42 which focuses the beam onto the specimen 41, which is movable in x and y directions (that is, along both the x and y coordinates at right angles to each other in a plane perpendicular to the microscope axis). The lens 418 is movable in the direction of all three coordinates, that is, in the x, y, and z directions. A filter 421 is arranged in front of the lens 418.

A lamp 420 is provided for illuminating the object or specimen 41. Light from this source 420 passes through the light collector or condenser lens 419 and through the beam splitter 417, and thence along the same path previously mentioned for passage of the laser beam, via the elements 415, 43, and 42 to the specimen 41.

The fluorescent light coming from the specimen is measured in broad band with a photomultiplier 414, or is recorded, after spectral dispersion with the aid of a monochromator (not shown) by a multichannel detector system. Within the radiation ray path there is a field diaphragm 416 as mentioned above, and within the fluorescent ray path there is a cutoff filter 44.

The laser microscope is provided with another beam splitter 45 which, for the purpose of direct observation, deflects a portion of the fluorescent light coming from the specimen to a lens 46 and thence to an eyepiece 47 and into the eye 48 of an observer. The microscope also has a lens 49 which focuses the fluorescent light at the locus of the measurement diaphragm 410 in front of the photomultiplier 414.

Figure 5:
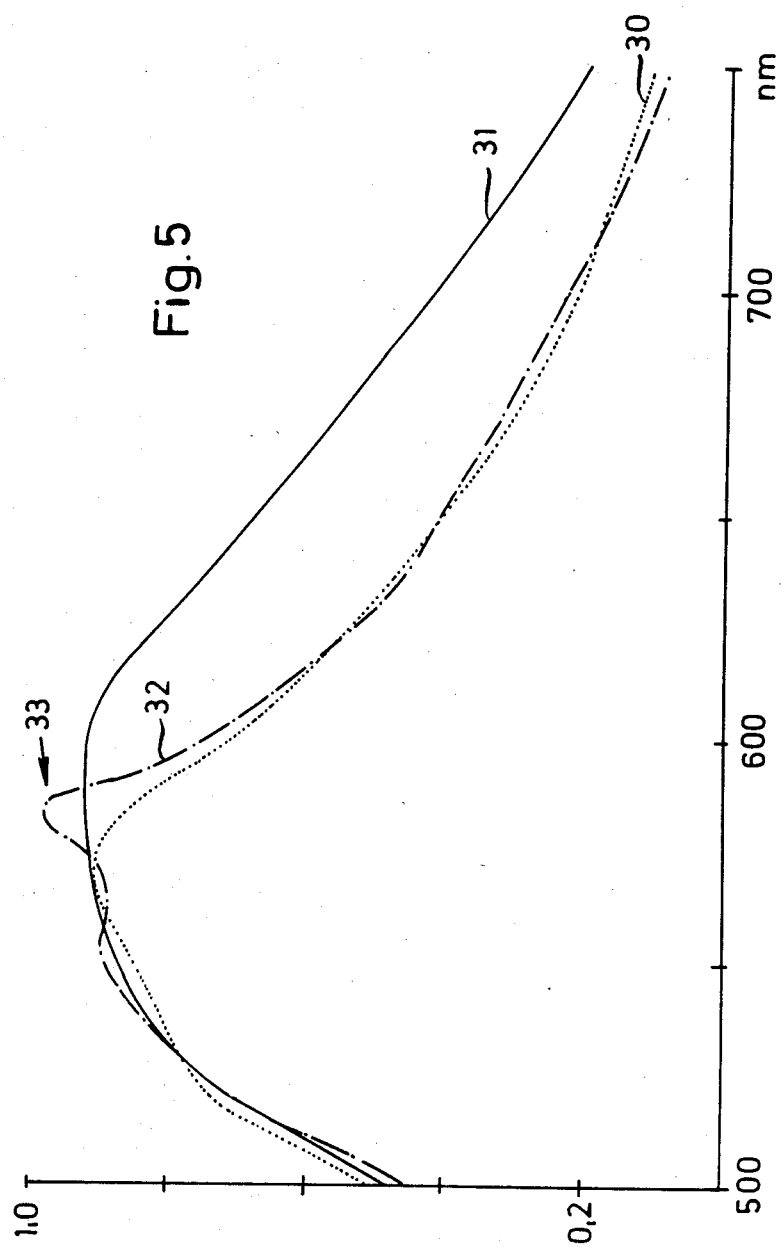
FIG. 5 is a graph showing the fluorescence spectra of blood at the start and at the end of the coagulation.

FIG. 5 shows a graphic form the results of measurement of the relative intensity of fluorescent radiation, plotted on the ordinate axis or vertical axis, as a function of the wavelength of the fluorescent radiation (expressed in nm units) plotted on the abscissa or horizontal axis. The dotted line curve 30 refers to whole blood at the start of the coagulation, the full line curve 31 represents whole blood after the end of the coagulation, and the dot-dash line curve 32 refers to hemoglobin $10^{-3}$ molar in water. The arrow 33 indicates the Raman band.

The fluorescent spectrum of whole blood agrees substantially with the spectrum of pure hemoglobin at the beginning of the coagulation process. The wide band at 570 nm in the spectrum of hemoglobin corresponds to a Raman vibration band of the solvent, water. It is not present in whole blood. During the coagulation process, the fluorescent spectrum becomes wider. This can also be noted visually by the change from a greenish color impression to a yellowish color impression.

Figure 6:
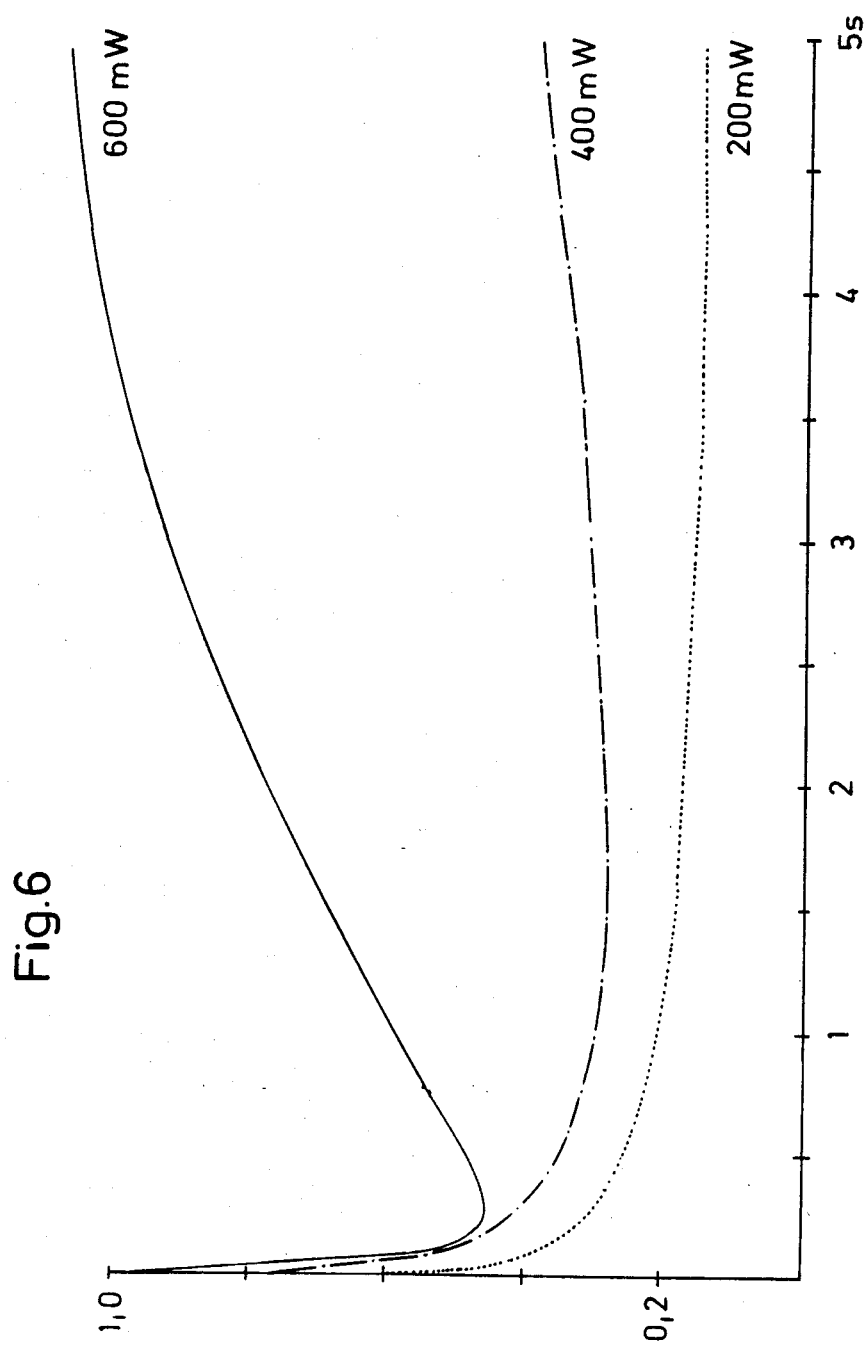
FIG. 6 is a graph showing the variation with time of the intensity of fluorescence of blood as a function of the laser output.

FIG. 6 shows the variations in the intensity of fluorescence with the passage of time, and the effect thereon of different strengths of irradiation. Intensity of fluorescence is plotted on the vertical ordinate axis, and time on the abscissa axis. As shown by the legends on the curves, the solid line curve represents results of a laser output of 600 mW, the dot-dash curve an output of 400 mW, and the dotted curve an output of 200 mW. It will be noted that the intensity of fluorescence decreases rapidly, depending on the strength of irradiation, passes through a minimum, and then rises slowly to a given final value. This minimum is particularly pronounced with higher laser output. As shown, with a laser output of 600 mW, the minimum is reached at the end of about 0.2 second. At this time, the widening of the fluorescent spectrum also commences, which also indicates a termination of the coagulation process.

Distinguishing the place of origin of the fluorescence is also possible by multi-band detection of the fluorescence.

Figure 7:
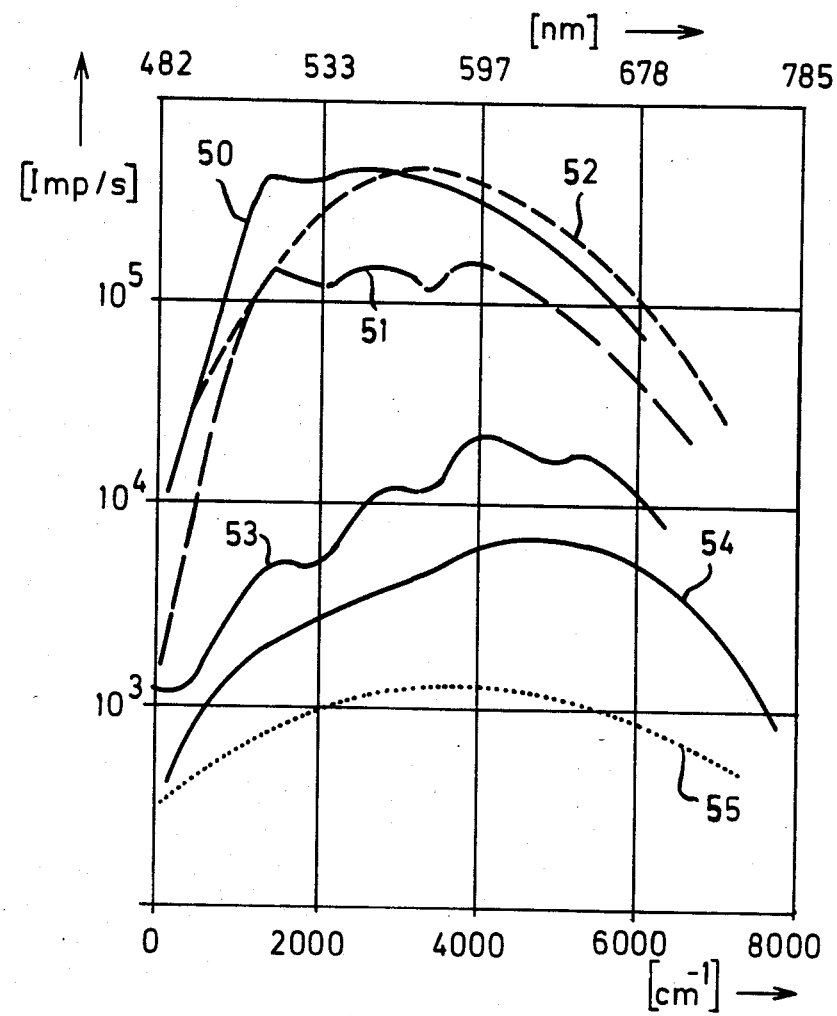
FIG. 7 is a graph summarizing and comparing the fluorescence spectra of differently treated blood sera.

FIG. 7 is a composite graph illustrating the fluorescence spectra of a number of different substances. The curve 50 applies to blood serum colored light yellow,
51 to blood serum colored red by hemolysis,
52 to urine,
53 to dilute and hemolyzed citrate blood, and 54 to bilirubin in CCl$_4$.

This FIG. 7 shows the recorded intensity in pulses per second (ordinate axis) in relation to frequency shift in cm$^{-1}$, (abscissa axis) without correction of the absorption or of the sensitivity of spectral detection. By way of comparison, there is shown the spectral course of the sensitivity of detection 55, referring to the laser intensity in mW, in arbitrary units.

What is claimed is:

1. Apparatus for producing photocoagulation at the fundus of an eye by means of laser radiation, comprising:
   (a) a laser radiation source for producing a beam of therapy radiation;
   (b) means for directing said beam of therapy radiation from said source to the fundus of an eye;
   (c) a first photodetector;
   (d) a first beam splitter located in said beam for directing part of said beam to said first photodetector to be measured thereby;
   (e) a shutter located in said beam for controlling passage or stoppage of said beam of therapy radiation;
   (f) radiation of the fundus of the eye by said beam of therapy radiation serving to produce fluorescence at said fundus, thereby producing a return beam of fluorescent radiation emanating from said fundus;
   (g) a second photodetector;
   (h) a second beam splitter located in said return beam for directing part of said return beam of fluorescent radiation to said second photodetector to be measured thereby;
   (i) a cutoff filter located in said return beam; and
   (j) means controlling said shutter jointly by output from said first photodetector integrated with respect to time and output from said second photodetector differentiated with respect to time.

2. The invention defined in claim 1, further comprising a third beam splitter located in said return beam to provide from said return beam an observation beam for direct observation of the effect of the therapy beam on the fundus.

3. The invention defined in claim 2, wherein said third beam splitter comprises a mirror (6) having a hole therethrough.

4. Apparatus for producing photocoagulation at the fundus of an eye by means of laser radiation, comprising:
   (a) a laser radiation source for producing a beam of therapy radiation;
   (b) means for directing said beam of therapy radiation from said source to the fundus of an eye;
   (c) a first photodetector;
   (d) a first beam splitter located in said beam for directing part of said beam to said first photodetector to be measured thereby;
   (e) a shutter located in said beam for controlling passage or stoppage of said beam of therapy radiation;
   (f) radiation of the fundus of the eye by said beam of therapy radiation serving to produce fluorescence at said fundus, thereby producing a return beam of fluorescent radiation emanating from said fundus;
   (g) a second photodetector;
   (h) means for directing part of said return beam of fluorescent radiation to said second photodetector to be measured thereby;
   (i) a cutoff filter located in said return beam; and
   (j) means controlling said shutter jointly by output from said first photodetector integrated with respect to time and output from said second photodetector differentiated with respect to time.

5. The invention defined in claim 4, wherein said means for directing said beam of therapy radiation to said fundus includes a glass fiber guide (14).

6. The invention defined in claim 5, wherein said glass fiber guide serves also as a guide for said return beam of fluorescent radiation.

* * * * *